(12) United States Patent
Joshi (10) Patent No.: US 8,267,906 B2
(45) Date of Patent: Sep. 18, 2012

(54) TRANSDERMAL DELIVERY APPARATUS AND METHOD

(75) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 0 days.

(21) Appl. No.: 12/950,131

(22) Filed: Nov. 19, 2010

(65) Prior Publication Data

US 2011/0064823 A1 Mar. 17, 2011

Related U.S. Application Data

(62) Division of application No. 12/163,698, filed on Jun. 27, 2008, now abandoned.

(51) Int. Cl.
*A61M 35/00* (2006.01)
*A61K 9/22* (2006.01)

(52) U.S. Cl. .................................. 604/290; 604/890.1

(58) Field of Classification Search ............ 604/289, 604/290, 304, 307, 890.1
See application file for complete search history.

(56) References Cited

U.S. PATENT DOCUMENTS

| | | | |
|---|---|---|---|
| 3,774,589 A | 11/1973 | Kober | |
| 3,980,070 A | 9/1976 | Krupa | |
| 4,067,313 A | 1/1978 | Donnelly | |
| 4,205,957 A | 6/1980 | Fijuwara | |
| 4,230,105 A | 10/1980 | Harwood et al. | |
| 4,522,190 A | 6/1985 | Kuhn et al. | |
| 4,963,360 A | 10/1990 | Arguad et al. | |
| 5,233,981 A | 8/1993 | Miyashita | |
| 6,019,782 A | 2/2000 | Davis et al. | |
| 6,096,067 A | 8/2000 | Cramer et al. | |
| 6,245,347 B1 | 6/2001 | Zhang et al. | |
| 6,261,595 B1 | 7/2001 | Stanley et al. | |
| 6,303,142 B1 | 10/2001 | Zhang et al. | |
| 6,306,431 B1 | 10/2001 | Zhang et al. | |
| 6,336,935 B1 | 1/2002 | Davis et al. | |
| 6,340,472 B1 | 1/2002 | Zhang et al. | |
| 6,465,006 B1 | 10/2002 | Zhang et al. | |
| 6,488,959 B2 | 12/2002 | Stanley et al. | |
| 6,756,053 B2 | 6/2004 | Zhang et al. | |
| 6,780,426 B2 | 10/2004 | Zhang et al. | |
| 6,890,553 B1 | 5/2005 | Sun et al. | |
| 6,920,873 B2 | 7/2005 | Venkatesan et al. | |
| 2008/0118417 A1 | 5/2008 | Mallory | |

OTHER PUBLICATIONS

Campbell, Victoria P., "USPTO Office Action", U.S. Appl. No. 12/163,698, (Aug. 31, 2010),1-9.

(Continued)

*Primary Examiner* — Victoria P Shumate
(74) *Attorney, Agent, or Firm* — David Fonda (57) ABSTRACT

An apparatus and method for applying a beneficial agent to the skin is disclosed in one embodiment of the invention as including first and second chemical reactants, each being compatible with the skin. The first and second chemical reactants react with one another to generate a beneficial agent and enhance the permeability of the skin (e.g., by generating heat). The beneficial agent may then be applied to the skin while the permeability of the skin is enhanced. In selected embodiments, the first chemical reactant includes one or more metals, or alloys thereof, that are compatible (i.e., not harmful) with the skin. Similarly, in selected embodiments, the second chemical reactant may include water. In certain embodiments, the beneficial agent generated by the first and second chemical reactants includes an antioxidant such as hydrogen.

18 Claims, 3 Drawing Sheets

OTHER PUBLICATIONS

Campbell, Victoria P., "USPTO Office Action", U.S. Appl. No. 12/163,698, (Jan. 22, 2010),1-6.

Kim, Hee J., "International Search Report", App. No. PCT/US2009/04767, (Jun. 27, 2008),1-4.

Kim, Hee J., "Written Opinion of the International Searching Authority", App. No. PCT/US2009/047677, (Jun. 27, 2008),1-5.

Prausnitz, Mark R., "Microneedles for transdermal drug delivery", *Advanced Drug Delivery Reviews* vol. 56, (2004),581-587.

TRANSDERMAL DELIVERY APPARATUS AND METHOD

RELATED APPLICATIONS

This application is a divisional application of U.S. patent application Ser. No. 12/163,698 filed on Jun. 27, 2008 now abandoned and entitled Transdermal Apparatus and Method. This prior application is incorporated herein by reference.

FIELD OF THE INVENTION

This invention relates to apparatus and methods for transdermally delivering medicines and other beneficial agents through the skin of a patient.

BACKGROUND

Adhesive transdermal patches, which deliver drugs to a recipient by passively diffusing drugs through the recipient's skin, have been available for several decades. These patches are used to treat systemic illnesses and are the predominant transdermal drug delivery technology approved by the FDA. During the past several decades, transdermal patches have become a proven technology that offers significant benefits compared to other delivery techniques. For example, transdermal patches may provide a finer level of control when releasing drugs into a patient. This feature may provide a steady blood-level profile which may in turn reduce systemic side effects and improve efficacy compared to other delivery techniques. Transdermal patches may also be more user-friendly, convenient, and painless than other delivery techniques. For this reason, transdermal patches are typically associated with improved patient compliance.

There is currently a significant amount of research being dedicated to improving techniques for transdermally delivering drugs using transdermal patches. For example, research has shown that complex chemical enhancers may be incorporated into delivery systems to improve transdermal drug delivery. Other research has shown that physical phenomena such as electricity (iontophoresis), ultrasound (phono- or sonophoresis), or magnetism may be used in a transdermal device to improve drug delivery. A highly effective although simpler mechanism for improving transdermal drug absorption, however, is the application of heat.

Heat application may improve transdermal drug delivery by increasing the permeability of skin, blood vessel walls, and rate-limiting membranes. Heat may also improve transdermal drug delivery by increasing the circulation of body fluids. Heating the skin dilates pathways in the skin, increases thermodynamic drive, increases the kinetic energy and movement of particles in the treated area, and facilitates drug absorption into the vascular network. This may improve systemic delivery while decreasing localized delivery as drug molecules are transported away from the delivery site.

Currently, various patches are being marketed or developed to apply heat to the skin and thereby increase drug absorption. Some of these patches generate heat using exothermic chemical reactions while others use electric heating elements coupled to control devices. Many of these patches are more complex than they need to be and may require several components (e.g., separated drug and heater portions). Patches that use exothermic reactions to produce heat may use chemical reactants or produce reaction products that are incompatible with the skin, thereby requiring isolation from the skin. Other patches may fail to take advantage of exothermic chemical reactants or reaction products that may be beneficial to the skin or body.

In view of the foregoing, what are needed are apparatus and methods to enhance the transdermal delivery of medicines and other beneficial agents. More specifically, apparatus and methods are needed to reduce the complexity, and thus the cost, of current transdermal patches. Further needed are transdermal patches that use exothermic chemical reactants or produce reaction products that are compatible with the skin, and thus do not require isolation from the skin. Further needed are transdermal patches that can take advantage of exothermic chemical reactants or reaction products that may be beneficial to the skin or body.

SUMMARY OF THE INVENTION

Consistent with the foregoing and in accordance with the invention as embodied and broadly described herein, a method for applying a beneficial agent to the skin is disclosed in one embodiment of the invention as including providing first and second chemical reactants, each being compatible with the skin. The first and second chemical reactants react with one another to generate a beneficial agent and enhance the permeability of the skin (e.g., by generating heat). The beneficial agent may then be applied to the skin while the permeability of the skin is enhanced. In selected embodiments, the first chemical reactant includes one or more metals, or alloys thereof, that are compatible (i.e., not harmful) with the skin. These metals may include, for example, zinc, magnesium, aluminum, iron, calcium, or alloys or mixtures thereof. Similarly, in selected embodiments, the second chemical reactant may include water, which may also includes mixtures or solutions thereof (e.g., saline). In certain embodiments, the beneficial agent generated by the first and second chemical reactants includes an antioxidant such as hydrogen.

In selected embodiments, the method further includes applying a second beneficial agent to the skin while the permeability of the skin is enhanced. This second beneficial agent may include for example one or more antioxidants, analgesics, anesthetics, anti-arthritis drugs, anti-inflammatory drugs, anti-migraine drugs, cardiovascular medications, pain-killers, anti-smoking drugs, natural or synthetic hormones, anti-hypertension agents, anti-depressants, antibiotics, anti-cancer agents, antiemetics, anti-infectants, contraceptives, diabetes drugs, steroids, anti-allergy agents, anti-migraine agents, dieting agents, vitamins, minerals, herbs, nutritional supplements, or the like.

In another embodiment of the invention, a method for applying a beneficial agent to the skin may include providing a beneficial agent in physical contact with a first chemical reactant. The beneficial agent and first chemical reactant may both be compatible with skin. The first chemical reactant may then be reacted with a second chemical reactant, also compatible with the skin, to enhance the permeability of the skin. The beneficial agent may then be applied to the skin while the permeability of the skin is enhanced. The first chemical reactant may include one or more metals, or alloys thereof, that are compatible with the skin, such as zinc, magnesium, aluminum, iron, calcium, or alloys or mixtures thereof. The second chemical reactant may include water or mixtures or solutions thereof. The beneficial agent may include one or more antioxidants, analgesics, anesthetics, anti-arthritis drugs, anti-inflammatory drugs, anti-migraine drugs, cardiovascular medications, pain-killers, anti-smoking drugs, natural or synthetic hormones, anti-hypertension agents, anti-depressants, antibiotics, anti-cancer agents, antiemetics, antiinfectants, contraceptives, diabetes drugs, steroids, anti-allergy agents, anti-migraine agents, dieting agents, vitamins, minerals, herbs, nutritional supplements, or the like.

In certain embodiments, the method may further include applying a second beneficial agent, generated from the reaction between the first and second chemical reactants, to the skin while the permeability of the skin is enhanced. In certain embodiments, the second beneficial agent includes an antioxidant such as hydrogen.

In another embodiment in accordance with the invention, an apparatus for applying a beneficial agent to the skin may include a housing and a first chemical reactant stored within the housing. The first chemical reactant is compatible with the skin and generates a beneficial agent and enhances the permeability of the skin when combined with a second chemical reactant. An application mechanism, which may include, for example direct contact, a permeable membrane, apertures, micro-needles, or the like, may be used to apply the beneficial agent to the skin while the permeability of the skin is enhanced.

In another embodiment in accordance with the invention, an apparatus for applying a beneficial agent to the skin may include a housing and a beneficial agent and a first chemical reactant stored together within the housing. The beneficial agent and first chemical reactant may both be compatible with the skin. The first chemical reactant enhances the permeability of the skin when combined with a second chemical reactant. An application mechanism may be provided to apply the beneficial agent to the skin while the permeability of the skin is enhanced.

In yet another embodiment of the invention, an apparatus for applying beneficial agents to the skin may include a housing and a first beneficial agent and a first chemical reactant stored together within the housing. The first beneficial agent and first chemical reactant are both compatible with the skin. The first chemical reactant is selected to generate a second beneficial agent and enhance the permeability of the skin when combined with a second chemical reactant. An application mechanism is provided to apply the first beneficial agent and the second beneficial agent to the skin while the permeability of the skin is enhanced.

The present invention provides improved apparatus and methods for applying beneficial agents to the skin. The features and advantages of the present invention will become more fully apparent from the following description and appended claims, or may be learned by practice of the invention as set forth hereinafter.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings in which.

DETAILED DESCRIPTION OF THE INVENTION

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following description, numerous specific details are presented to provide a thorough understanding of embodiments of the invention. One skilled in the relevant art will recognize, however, that the invention can be practiced without one or more of the specific details, or with other methods, components, materials, and so forth. In other instances, well-known structures, materials, or operations such as vacuum sources are not shown or described in detail to avoid obscuring aspects of the invention.

For the purposes of this description, the term "transdermal" may be used not only to refer to drugs or beneficial agents absorbed through the skin, but also to beneficial agents (e.g., moisturizers, drugs, etc.) applied inside (i.e., intradermal) or to the surface of the skin. Similarly, the phrase "beneficial agent," unless noted otherwise, may be used generally to refer to various substances such as antioxidants, analgesics, anesthetics, anti-arthritis drugs, anti-inflammatory drugs (e.g., ketoprofen), anti-migraine drugs, cardiovascular medications, pain-killers, anti-smoking drugs, natural or synthetic hormones, anti-hypertension agents, anti-depressants, antibiotics, anti-cancer agents, antiemetics, anti-infectants, contraceptives, diabetes drugs, steroids, anti-allergy agents, anti-migraine agents, dieting agents, vitamins, health supplements, minerals, herbs, or the like. Furthermore, the term "applying" may include applying to the surface of the skin, applying transdermally through the skin, applying intradermally within the skin, or combinations thereof. The term "skin" is used to refer to mammalian skin.

Figure 1:
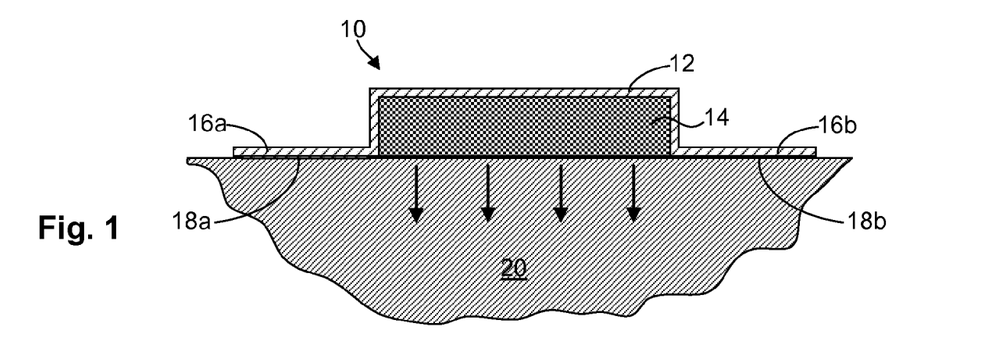
FIG. 1 is a high-level diagram of one embodiment of a patch for applying beneficial agents to the skin.

Referring to FIG. 1, as mentioned previously, transdermal drug delivery provides various advantages over other delivery techniques (e.g., oral or intravenous delivery techniques, etc.). In order to be effective, a transdermal delivery technique must be able to penetrate the primary barrier to drug delivery—the skin. The skin is composed of three layers, the epidermis, dermis, and hypodermis. The epidermis (i.e., the outermost layer of skin) is the most substantial barrier to drug diffusion. As previously mentioned, heat may be applied to the skin to increase the skin's ability to absorb beneficial agents.

Recent studies have also shown that reactive oxygen species (i.e., "free radicals") can be very harmful to the skin and may be the primary cause of skin cancer. Ultraviolet radiation, and in particular UVA and UVB radiation, are known to create free radicals upon contacting the skin. These free radicals can alter the structure of RNA, DNA, proteins, and fat in skin cells until they eventually cause cancer. For this reason, some advocate infusing the skin with antioxidants, by diet or other means, to counteract the effects of free radicals. These antioxidants may protect cells by reacting with or otherwise neutralizing free radicals. In view of the foregoing, it would be an advance in the art to provide a transdermal patch that could not only deliver heat and beneficial agents through the skin, but also infuse the skin with antioxidants.

In selected embodiments, an apparatus 10 in accordance with the invention may include a housing 12 containing a mixture 14 of one or more chemical reactants that are compatible with the skin, and optionally one or more beneficial agents for delivery on or through the skin. Although not always necessary, the apparatus 10 may in certain embodiments include tabs 16a, 16b, extensions 16a, 16b, or the like to secure the apparatus 10 to a user's skin. These extensions 16a, 16b may include an adhesive 18a, 18b to provide a suitable bond with the skin. The apparatus 10 may be provided in various shapes and forms (e.g., circular, oval-shaped, rectangular, etc.) as desired. It will be appreciated that the apparatus may be in the form of a patch 10 and that patch and apparatus may be used interchangeably throughout the specification. It will further be appreciated that the housing 12 may be in form of a support structure and the housing 12 is not necessarily a container wherein the mixtures, beneficial agents, or reactants are always contained therein. In some embodiments, the housing 12 or support structure 12 may support the components of the apparatus 10 within or outside of the housing 12.

The chemical reactants in the mixture 14 may generate heat when combined with other chemical reactants, in this example water or aqueous solutions or mixtures thereof. In certain embodiments, the water (or aqueous solutions or mixtures thereof) may be applied to the patch 10 by dipping, spraying, rinsing, or otherwise wetting the patch 10 when it is ready for use. Thus, the housing 12 may be made from a permeable or semi-permeable material to enable water to penetrate the housing 12 and contact the chemical reactants 14. In other embodiments, as will be explained in association with FIG. 8, the water may be contained within the patch 10 but may be isolated from other chemical reactants until the patch 10 is ready for use.

In selected embodiments, the chemical reactants in the mixture 14 may include various metal powders such as powders of zinc, magnesium, aluminum, iron, calcium, or mixtures or alloys thereof. These metals have the benefit that they are compatible with the skin, will exothermically react with water, and generate a reaction product that is also compatible with the skin. They also have the benefit that they will produce hydrogen, a powerful antioxidant, when reacted with water.

For example, if zinc powder is provided in the mixture 14, the zinc may react with water to form zinc oxide (a skin-compatible reaction product) and hydrogen in accordance with the following equation:

$$Zn+H_2O \rightarrow ZnO+H_2$$

This reaction also produces heat. The amount of heat and hydrogen produced may be adjusted by controlling the speed of the reaction. As will be explained in more detail hereafter, the speed of the reaction may be controlled by altering various characteristics of the metal powder or by mixing or alloying the metal powder with other materials, adding enhancing agents, or the like. Like zinc, powders of magnesium, aluminum, iron, calcium, will also react with water to form hydrogen and skin-compatible reaction products (i.e., magnesium oxide, aluminum oxide, iron oxide, and calcium hydroxide).

Because the metal powders discussed above are compatible with the skin and produce reaction products that are also compatible with the skin, there is a reduced need to isolate these products from the skin. As a result, the hydrogen produced by these metals may be beneficially applied to the skin. Hydrogen gas is particularly effective as an antioxidant because it is such a small molecule. Consequently, hydrogen may achieve more intimate contact with free radicals in the skin and thus may be particularly effective at taking up and neutralizing free radicals. Thus, in selected embodiments, chemical reactants that generate hydrogen may be particularly desirable.

As mentioned, the mixture 14 may also contain one or more beneficial agents such as medications, drugs, vitamins, minerals, health supplements, hormones, contraceptives, or the like. Although not mandatory, in selected embodiments these beneficial agents may be mixed or intermingled with the chemical reactants in the mixture 14. This may provide more uniform heating of the skin and the beneficial agents in the mixture 14 to provide improved absorption through the skin.

This may also reduce the number of components required for the patch 10 by reducing the need to have separate isolated compartments to provide heat and beneficial agents. This may reduce costs and improve the feasibility of providing an entirely disposable patch.

As shown in FIG. 1, in selected embodiments, the patch 10 may be designed such that the mixture 14 containing the chemical reactants and the beneficial agents is placed in direct contact with the skin 20. This may be accomplished, for example, by providing a mixture 14 that is solid or substantially solid (such as a compressed tablet), or providing a carrier material saturated with a liquid or gaseous beneficial agent. As the mixture 14 is heated by reacting the chemical reactants, the beneficial agents as well as the hydrogen produced by the chemical reaction may diffuse through the skin 20.

To control the speed of the reaction, and thus the amount of heat and hydrogen generated by the patch 10, various characteristics of the chemical reactants may be altered. For example, a metal powder with a finer particle size will increase the total surface area of the metal powder and accelerate the reaction. The type of metal powder may also affect the reaction speed. For example, for a given particle size, magnesium and calcium will react with water faster than zinc. Thus, metals with different reaction speeds may be used or mixed together in different proportions to tailor the overall reaction speed. In some embodiments, metals may be alloyed together to alter the reaction speed and thus the amount of heat and hydrogen produced.

In other embodiments, conductive elements may be intermixed or placed in contact with the metal powders to alter the reaction speed. For example, carbon or silver may be mixed with the metal powders to facilitate the flow of electrons through the mixture 14. As the metal powders react, electrons are exchanged as they form stable oxides and hydroxides. These oxides and hydroxides are typically insulators that will build up in the mixture 14 and on the surface of the metal particles, thereby impeding the flow of electrons and slowing the reaction. Carbon powder or other inert conductive powders such as silver powder may be combined with the mixture 14 to facilitate electron flow and maintain or accelerate the reaction speed. In other embodiments, impurities such as lead may be added to the mixture 14 to slow the reaction. Thus, the materials and characteristics of the materials in the mixture 14 may be altered to tailor the reaction speed.

Figure 2:
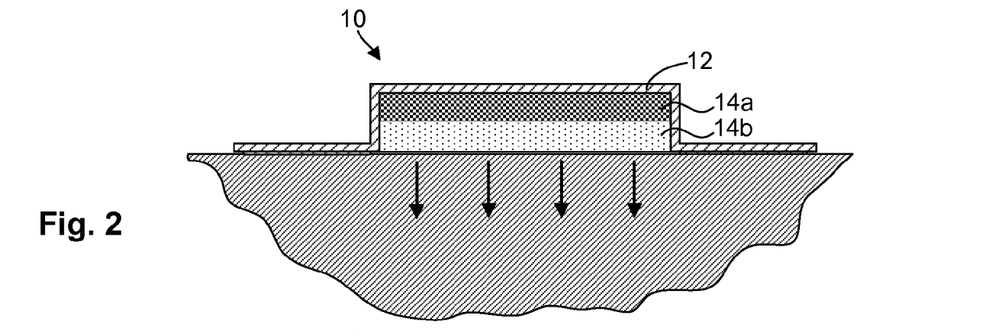
FIG. 2 is a high-level diagram of another embodiment of a patch for applying beneficial agents to the skin.

Referring to FIG. 2, in other contemplated embodiments, instead of providing a mixture 14 as illustrated in FIG. 1, various constituents may be placed physically adjacent to one another. For example, the heat- and hydrogen-producing chemical reactants 14a may be placed adjacent to beneficial agents 14b. This may place more of the beneficial agents adjacent to the skin. Furthermore, hydrogen generated by the chemical reactants 14a may permeate through or around the beneficial agents 14b to be absorbed by the skin since hydrogen is a very small molecule. Thus, as illustrated in FIGS. 1 and 2, the chemical reactants and beneficial agents may be provided in different arrangements and with different levels of granularity, as desired.

Figure 3:
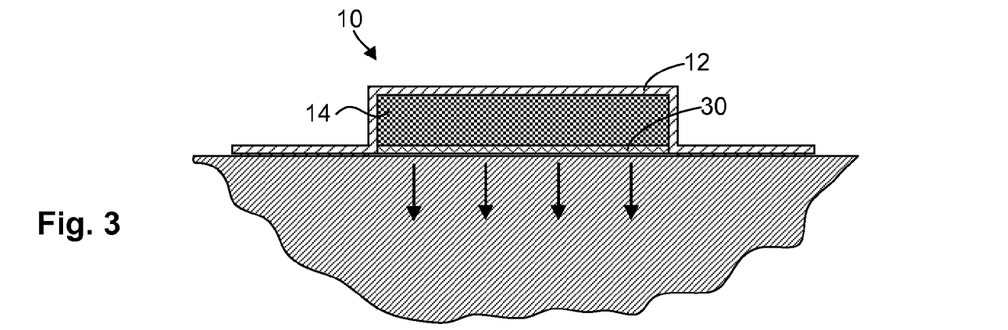
FIG. 3 is a high-level diagram of one embodiment of a patch using a permeable membrane to apply beneficial agents to the skin.

Referring to FIG. 3, in other embodiments, a membrane 30 such as a semi-permeable membrane or selectively permeable membrane may be used to enable diffusion of selected chemicals or beneficial agents through the membrane 30 for absorption by the skin. For example, a membrane 30 may be provided to enable diffusion of hydrogen, water, and beneficial agents but would keep chemical reactants or reaction products such as metal, oxide, or hydroxide particles within the patch 10. In other embodiments, water may also be retained within the patch 10. The membrane 30 may be selected such that the rate of diffusion depends on one or more of pressure, concentration, temperature, or the type of molecules or solutes on either side of the membrane 30.

Figure 4:
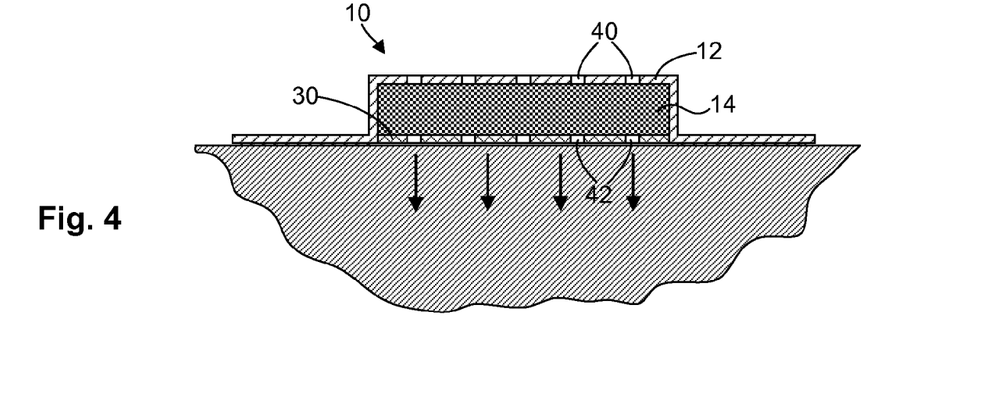
FIG. 4 is a high-level diagram of one embodiment of a patch having apertures formed in various surfaces thereof.

Referring to FIG. 4, in other embodiments, apertures 40, 42 of varying sizes may be provided in the housing 12, a membrane 30, or both. For example, apertures 40 may be provided in the housing 12 to allow water to enter the patch 10 (by dipping, rinsing, spraying, etc.) to activate the patch 10. The apertures 40 may be sized to allow water to enter the patch 10 while preventing chemical reactants inside the patch 10 from leaking from the patch 10. Thus, the size of the apertures 40 may depend on the size of particles or other constituents within the patch 10. In certain embodiments, the housing 12 may be fabricated from a fibrous material such as fabric, paper, or other fiber-based material and the apertures 40 may simply be the space between the fibers. In other embodiments, the apertures 40 may be provided in the form of perforations in plastic, latex, fabric, or the like.

Similarly, apertures 42 may be provided in a bottom surface of the patch 10 to allow hydrogen, water, or other beneficial agents to diffuse through the bottom surface into the skin. The apertures may be sized to allow one or more of hydrogen, beneficial agents, and water to diffuse through the bottom surface, while keeping other constituents such as metal, oxide, or hydroxide particles within the patch 10. In certain embodiments, the apertures 42 are simply space between the fibers of materials such as fabric, paper, meshes, screens, or other media or are apertures 42 formed in materials such as plastic, latex, fabric, or the like.

Figure 5:
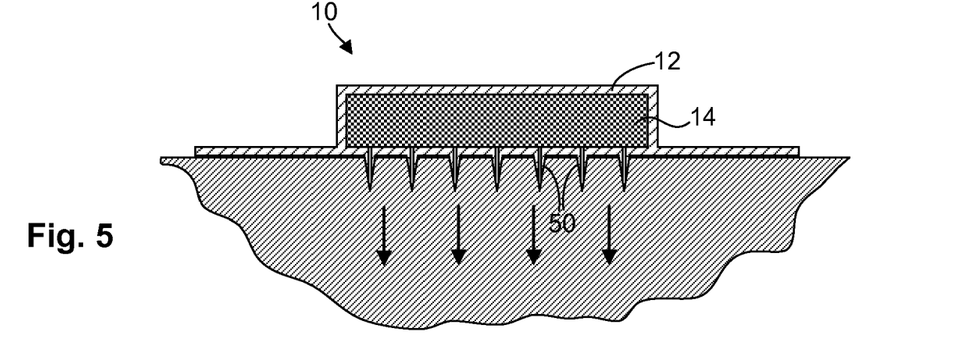
FIG. 5 is a high-level diagram of one embodiment of a patch using micro-needles to inject beneficial agents through the skin.

Referring to FIG. 5, in other embodiments, a patch 10 in accordance with the invention may include hollow micro-needles 50 positioned on an underside thereof. The micro-needles 50 may communicate with hydrogen, beneficial agents, and/or water inside the patch 10. In selected embodiments, the micro-needles 50 may be provided in a dense array on the underside of the patch 10 and may have widths on the order of microns and lengths of less than one millimeter up to several millimeters. In one embodiment the micro-needles have a width ranging between about 1 and about 200 microns. In another embodiment, the micro-needles have a width ranging between about 50 and about 100 microns. In one embodiment, the micro-needle has a length of up to about 1 millimeter. These micro-needles 50 may decrease the amount of pain experienced by a patient using conventional needles as they may penetrate only the outermost layer of skin.

One benefit of producing hydrogen and heat with various embodiments of the patch 10 described herein is that it may increase the pressure within the patch 10. This may be used beneficially to pump fluids, such as hydrogen, beneficial agents, or water through a membrane 30, apertures 42, or micro-needles 50. In selected embodiments, the housing 12 may be provided with a hard wall such that its volume does not change substantially upon experiencing a pressure increase, thereby helping pump the fluids.

Figure 6:
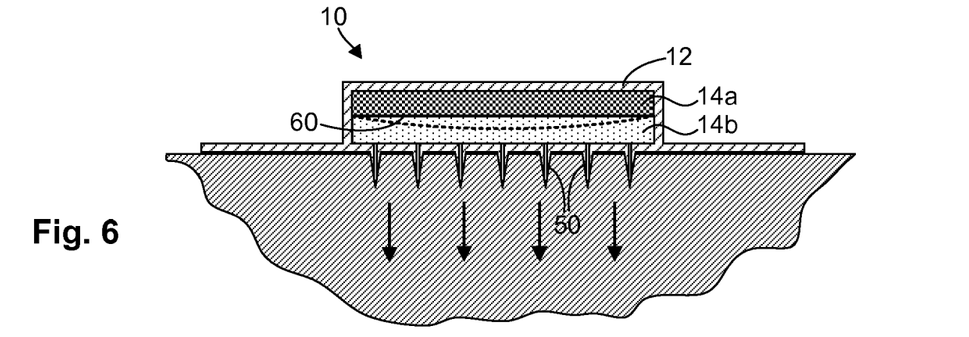
FIG. 6 is a high-level diagram of another embodiment of a patch using micro-needles to inject beneficial agents through the skin.

Referring to FIG. 6, in other contemplated embodiments, a patch 10 may be partitioned such that chemical reactants 14a may be separated from beneficial agents 14b using a flexible membrane 60. Upon reacting the chemical reactants 14a (e.g., metal powder with water), pressure may be generated which may urge the membrane 60 downward (as indicated by the dotted line), pumping the beneficial agents 14b through the micro-needles 50 (or alternatively a membrane 30 or apertures 42). In selected embodiments, the membrane 60 may be a semi-permeable membrane 60 to allow hydrogen to slowly diffuse through the membrane 60 for delivery to the skin.

Figure 7:
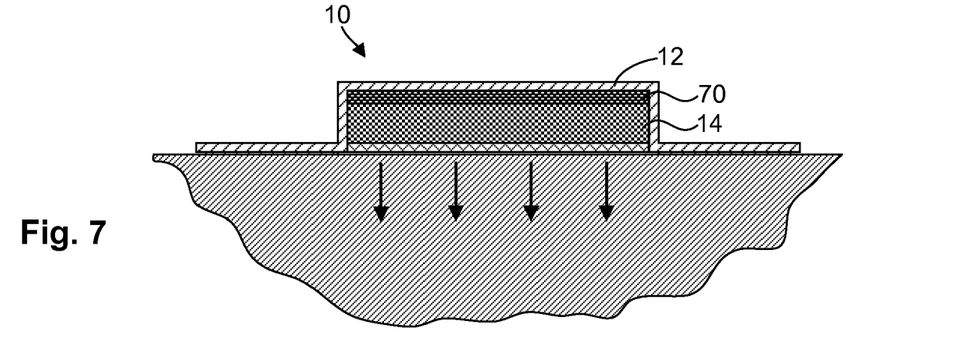
FIG. 7 is a high-level diagram of one embodiment of a patch using a carbon layer to accelerate a reaction within the patch.

Referring to FIG. 7, in other embodiments, a patch 10 in accordance with the invention may include various components or materials to accelerate the chemical reaction. For example, carbon felt 70 or other carbon or silver media may be placed around or adjacent to the chemical reactants 14 (e.g., metal powder and water) to facilitate the flow of electrons therethrough. The carbon media 70 may increase the reaction speed of materials such as zinc, which normally reacts very slowly with water.

Figure 8:
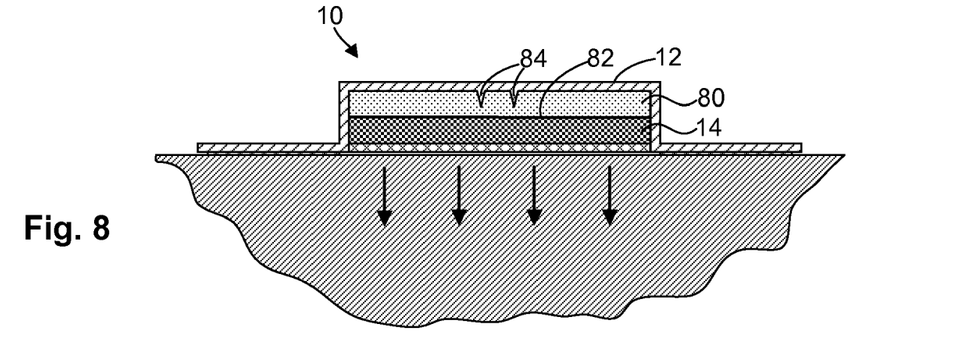
FIG. 8 is a high-level diagram of one embodiment of a patch storing water to activate the patch.

Referring to FIG. 8, in selected embodiments, a patch 10 in accordance with the invention may store all of the chemical reactants required to generate heat and/or hydrogen. For example, the patch 10 may include a first partition 14 storing chemical reactants, such as metal powders, and one or more beneficial agents such as medicines, drugs, vitamins, minerals, health supplements, hormones, contraceptives, or the like. A second partition 80 may store water or other aqueous mixture or solutions. A membrane 82 or separator 82 may separate the partitions 14, 80. To activate the patch 10, a user may puncture or remove the membrane 82, allowing the water 80 to mix with and react with the metal powder 14 to generate heat and/or hydrogen. In selected embodiments, a puncture mechanism, such as one or more spikes 84 may be provided to puncture the membrane 82 upon applying pressure to an upper surface of the housing 12. Thus, in selected embodiments, the patch 10 may be fully self-contained to include all required chemical reactants.

Figure 9:
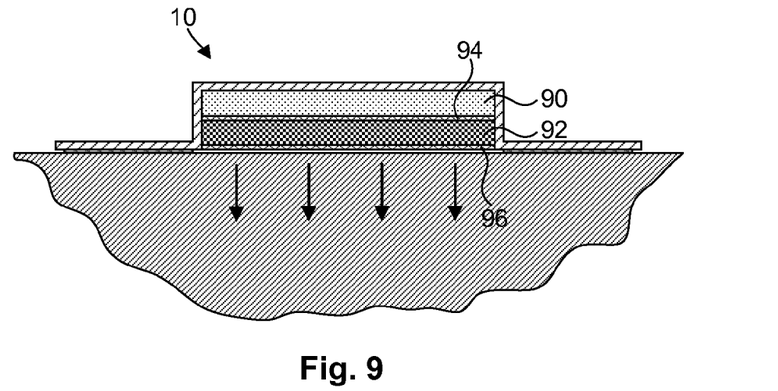
FIG. 9 is a high-level diagram of one embodiment of a patch generating multiple beneficial agents.

Referring to FIG. 9, in another embodiment, a patch 10 in accordance with the invention may generate multiple beneficial agents for application to the skin. For example, a first compartment 90 may store a metal powder such as zinc powder. This zinc powder may generate heat and hydrogen when combined with water. The hydrogen may diffuse into a second compartment 92 through a hydrogen-permeable membrane 94. The second compartment 92 may store an oxygen-generating compound such as magnesium peroxide ($MgO_2$) powder. This powder may generate oxygen, an effective wound-healing agent, when combined with water, in accordance with the following equation:

$$MgO_2 + H_2O \rightarrow MgO + H_2O + \tfrac{1}{2}O_2$$

Hydrogen, oxygen, as well as moisture in the second compartment 92 may diffuse through a permeable membrane 96 for absorption by the skin. Furthermore, heat generated in the first compartment 90 may enhance the permeability of the skin, thereby improving absorption.

Figure 10:
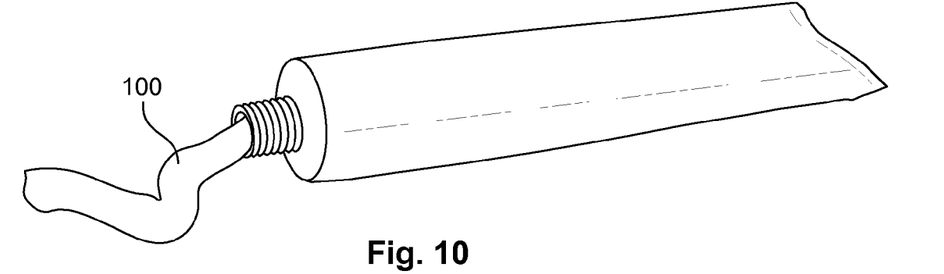
FIG. 10 shows one embodiment of a topical product such as a cream or lotion that may be used to implement a method in accordance with the invention.

Referring to FIG. 10, in selected embodiments, a topical product 100 for implementing a method in accordance with the invention may include a cream, lotion, ointment, or other topical preparation for application to the skin. In selected embodiments, the topical product 100 may contain one or more chemical reactants, such as one or more of the metal powders (or an oxygen-generating compound) as described above, suspended in a vehicle such as a cream or other topical preparation. The topical product 100 may also contain one or more beneficial agents. When a user wishes to utilize the topical product 100, the user may combine the topical product 100 with a small amount of water in the hand or other container and apply the product 100 to the skin. The water will react with the metal powders to generate heat and hydrogen (and possibly oxygen if an oxygen-generating compound is included) for application to the skin. The heat will also improve the permeability of the skin and thereby help the skin absorb the hydrogen, oxygen, beneficial agents, and/or moisture. The metal powder and water will generate reaction products (e.g., zinc oxide, magnesium oxide, aluminum oxide, iron oxide, calcium hydroxide, etc.) that are compatible with and potentially beneficial to the skin.

Figure 11:
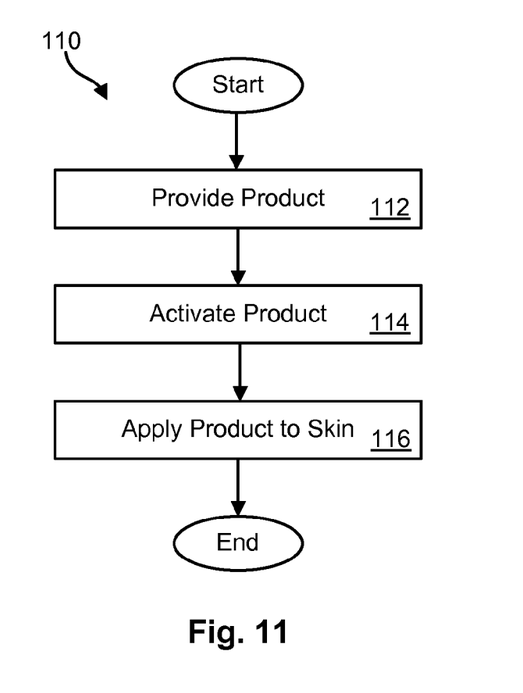
FIG. 11 is a flow chart showing one embodiment of a method for using a patch or topical product in accordance with the invention.

Referring to FIG. 11, a method 110 for using a patch 10 or topical product 100 in accordance with the invention may include initially providing 112 a product (e.g., a patch 10 or topical product 100) and activating 114 the product. Activating 114 may include initiating the heat- and/or hydrogen-producing chemical reaction by dipping, rinsing, spraying or otherwise wetting a patch 10 with water. In other embodiments, activating 114 may include puncturing or removing a membrane 82 of a patch 10, thereby allowing water to combine with other chemical reactants as illustrated in FIG. 8. In yet other embodiments, activating 114 may include mixing a topical product 100 with water to initiate a chemical reaction. Before, during, or after the product is activated 114, the product may be applied 116 to the skin. This may include applying 116 a patch 10 to the skin with an adhesive or other suitable attachment mechanism. In other embodiments, applying 116 may include piercing the skin with microneedles or other suitable injection means. In yet other embodiments, applying 116 may include rubbing a topical product 100 such as a cream or ointment onto the skin.

It should be recognized that the methods and apparatus discussed herein may be applied to a wide variety of products, each of which is intended to be captured within the scope of the present invention. For example, the apparatus and methods discussed in association with the patch 10 and topical product 90 could be applied to a wide variety of products including facial masks, body wraps, mud masks, sprays, bathing products, massage products, body powders, moisturizers, bandages, or the like.

The present invention may be embodied in other specific forms without departing from its basic principles or essential characteristics. The described embodiments are to be considered in all respects as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for applying a beneficial agent to the skin, the method comprising:
   providing a mixture comprising a first beneficial agent in physical contact with a first chemical reactant, the first beneficial agent and first chemical reactant both being compatible with skin, the first beneficial agent providing a beneficial effect upon being absorbed transdermally through the skin;
   adding a second chemical reactant, also compatible with the skin, to the mixture to react with the first chemical reactant and thereby generate heat; and
   applying the mixture to the skin while the mixture is generating heat, the heat enhancing the permeability of the skin to improve the absorption of the first beneficial agent transdermally through the skin.

2. The method of claim 1, wherein the reaction generates a second beneficial agent and the heat improves absorption of the second beneficial agent transdermally through the skin.

3. The method of claim 2, wherein the second beneficial agent is an antioxidant.

4. The method of claim 3, wherein the second beneficial agent is hydrogen.

5. The method of claim 1, wherein the first beneficial agent comprises at least one beneficial agent selected from the group consisting of antioxidants, analgesics, anesthetics, anti-arthritis drugs, anti-inflammatory drugs, anti-migraine drugs, cardiovascular medications, pain-killers, anti-smoking drugs, natural or synthetic hormones, antihypertension agents, anti-depressants, antibiotics, anti-cancer agents, antiemetics, antiinfectants, contraceptives, diabetes drugs, steroids, anti-allergy agents, anti-migraine agents, dieting agents, vitamins, minerals, and herbs.

6. The method of claim 1, wherein the first chemical reactant comprises at least one metal powder.

7. The method of claim 6, wherein the at least one metal powder comprises at least one of zinc, magnesium, aluminum, iron, and calcium powders.

8. The method of claim 1, wherein the second chemical reactant is water.

9. The method of claim 1, wherein the mixture is provided in the form of a topical product.

10. The method of claim 9, wherein the topical product is one of a cream, lotion, and an ointment.

11. A method for applying a beneficial agent to the skin, the method comprising:
providing a mixture comprising a first beneficial agent in physical contact with a first chemical reactant, the first beneficial agent and first chemical reactant both being compatible with skin, wherein the first chemical reactant is a metal powder, the first beneficial agent provides a beneficial effect upon being absorbed transdermally by the skin, and the first beneficial agent comprises at least one beneficial agent selected from the group consisting of antioxidants, analgesics, anesthetics, anti-arthritis drugs, anti-inflammatory drugs, anti-migraine drugs, cardiovascular medications, pain-killers, anti-smoking drugs, natural or synthetic hormones, anti-hypertension agents, anti-depressants, antibiotics, anticancer agents, antiemetics, anti-infectants, contraceptives, diabetes drugs, steroids, antiallergy agents, anti-migraine agents, dieting agents, vitamins, minerals, and herbs;
adding second chemical reactant, also compatible with the skin, to the mixture to react with the first chemical reactant and thereby generate heat; and
applying the mixture to the skin while the mixture is generating heat, the heat enhancing the permeability of the skin to improve the absorption of the first beneficial agent transdermally by the skin.

12. The method of claim 11, wherein the reaction generates a second beneficial agent and the heat improves absorption of the second beneficial agent transdermally by the skin.

13. The method of claim 12, wherein the mixture is provided in the form of a topical product.

14. The method of claim 12, wherein the second beneficial agent is an antioxidant.

15. The method of claim 14, wherein the second beneficial agent is hydrogen.

16. The method of claim 11, wherein the metal powder comprises at least one of zinc, magnesium, aluminum, iron, and calcium powders.

17. The method of claim 11, wherein the second chemical reactant is water.

18. A method for applying a beneficial agent to the skin, the method comprising:
providing a mixture comprising a first beneficial agent in physical contact with a first chemical reactant, the first beneficial agent and first chemical reactant both being compatible with skin, the first beneficial agent providing a beneficial effect upon being absorbed transdermally by the skin, the first reactant comprising at least one metal powder selected from the group consisting of zinc, magnesium, aluminum, iron, and calcium powders;
adding a second chemical reactant, also compatible with the skin, to the mixture to react with the first chemical reactant and thereby generate heat and a second beneficial agent, wherein the second chemical reactant comprises water; and
applying the mixture to the skin while the mixture generates heat, the heat enhancing the permeability of the skin to improve absorption of the first and second beneficial agents transdermally by the skin.

* * * * *